United States Patent
Lin et al.

(10) Patent No.: US 6,274,740 B1
(45) Date of Patent: Aug. 14, 2001

(54) **PROCESS FOR THE PRODUCTION OF AMORPHOUS [R-(R*,R*)]-2-(4-FLUOROPHENYL)-β, δ-DIHYDROXY-5-(1-METHYLETHY)-3-PHENYL-4-[(PHENYLAMINO) CARBONYL]-1H-PYRROLE-1-HEPTANOIC ACID CALCIUM SALT (2:1)**

(75) Inventors: Min Lin, Plainsboro, NJ (US); Dieter Schweiss, Holland, MI (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 09/657,469

(22) Filed: Sep. 7, 2000

Related U.S. Application Data

(62) Continuation of application No. 09/453,189, filed on Dec. 2, 1999, now abandoned, which is a continuation of application No. 08/983,369, filed as application No. PCT/US96/11807 on Jul. 16, 1996, now Pat. No. 6,087,511

(60) Provisional application No. 60/001,453, filed on Jul. 17, 1995.

(51) Int. Cl.[7] .................. C07D 207/335; C07D 207/34
(52) U.S. Cl. ............................................................. 548/537
(58) Field of Search ............................................. 548/537

(56) References Cited

U.S. PATENT DOCUMENTS

| | | | |
|---|---|---|---|
| 4,681,893 | 7/1987 | Roth | 514/422 |
| 5,003,080 | 3/1991 | Butler et al. | 548/517 |
| 5,097,045 | 3/1992 | Butler et al. | 549/373 |
| 5,103,024 | 4/1992 | Millar et al. | 549/373 |
| 5,124,482 | 6/1992 | Butler et al. | 564/169 |
| 5,149,837 | 9/1992 | Butler et al. | 549/333 |
| 5,155,251 | 10/1992 | Butler et al. | 558/442 |
| 5,216,174 | 6/1993 | Butler et al. | 548/517 |
| 5,245,047 | 9/1993 | Butler et al. | 548/517 |
| 5,248,793 | 9/1993 | Millar et al. | 548/375 |
| 5,273,995 | 12/1993 | Roth | 514/422 |
| 5,280,126 | 1/1994 | Butler et al. | 548/517 |
| 5,342,952 | 8/1994 | Butler et al. | 546/245 |
| 5,397,792 | 3/1995 | Butler et al. | 514/326 |
| 5,446,054 | 8/1995 | Butler et al. | 514/326 |
| 5,969,156 | 10/1999 | Briggs et al. | 548/357 |

FOREIGN PATENT DOCUMENTS

| | | |
|---|---|---|
| 0247633 | 12/1987 | (EP) . |
| 0330172 | 8/1989 | (EP) . |
| 0409281 | 1/1991 | (EP) . |
| 89/07598 | 8/1989 | (WO) . |
| 94/20492 | 9/1994 | (WO) . |

OTHER PUBLICATIONS

Kearney, et al., *Pharmaceutical Research*, vol. 10, No. 10, 1993, pp. 1461–1465.

Baumann, et al., *Tetrahedron Letters*, vol. 33, No. 17, pp. 2283–2284, 1992.

Konno, *Chem. Pharm. Bull.*, vol. 38, No. 7, pp. 2003–2007, 1990.

*Pharmaceutical Research*, vol. 10, No. 10, 1993, pp 1461–1465, Kearney, et al.

*Primary Examiner*—Jane C. Osweeki
(74) *Attorney, Agent, or Firm*—Francis J. Tinney

(57) ABSTRACT

A novel process for the preparation of amorphous atorvastatin is described where crystalline Form I atorvastatin is dissolved in a non-hydroxylic solvent and after removal of the solvent affords amorphous atorvastatin.

3 Claims, 3 Drawing Sheets

US 6,274,740 B1

PROCESS FOR THE PRODUCTION OF AMORPHOUS [R-(R*,R*)]-2-(4-FLUOROPHENYL)-β, δ-DIHYDROXY-5-(1-METHYLETHY)-3-PHENYL-4-[(PHENYLAMINO) CARBONYL]-1H-PYRROLE-1-HEPTANOIC ACID CALCIUM SALT (2:1)

This application is a continuation of U.S. Ser. No. 09/453,189 filed Dec. 2, 1999, abandoned, which is a continuation of U.S. Ser. No. 08/983,369 filed Jan. 15, 1998, now U.S. Pat. No. 6,087,511 issued Jul. 11, 2000, which is a §371 filing from PCT/US96/11807 filed Jul. 16, 1996, which claims priority from U.S. provisional application No. 60/001,453 filed Jul. 17, 1995.

BACKGROUND OF THE INVENTION

The present invention relates to a novel process for amorphous atorvastatin which is known by the chemical name [R—(R*,R*)]-2-(4-fluorophenyl)-β,δ-dihydroxy-5-(1-methylethyl)-3-phenyl-4-[(phenylamino) carbonyl]-1H-pyrrole-1-heptanoic acid hemi calcium salt which is useful as a pharmaceutical agent. Atorvastatin is useful as an inhibitor of the enzyme 3-hydroxy-3-methylglutaryl-coenzyme A reductase (HMG-COA reductase) and is thus useful as a hypolipidemic and hypocholesterolemic agent.

U.S. Pat. No. 4,681,893, which is herein incorporated by reference, discloses certain trans-6-[2-(3- or 4-carboxamido-substituted-pyrrol-1- yl)alkyl]-4-hydroxy-pyran-2-ones including trans (±)-5- (4-fluorophenyl)-2-(1-methylethyl)-N,4-diphenyl-1-[(2-tetrahydro-4-hydroxy-6-oxo-2H-pyran-2-yl)ethyl]-1H-pyrrole-3-carboxamide.

U.S. Pat. No. 5,273,995, which is herein incorporated by reference, discloses the enantiomer having the R form of the ring-opened acid of trans-5-(4-fluorophenyl)-2-(1-methylethyl)-N,4-diphenyl-1-[(2-tetrahydro-4-hydroxy-6-oxo-2H-pyran-2-yl)ethyl]-1H-pyrrole-3-carboxamide, i.e., [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid.

U.S. Pat. Nos. 5,003,080; 5,097,045; 5,103,024; 5,124,482; 5,149,837; 5,155,251; 5,216,174; 5,245,047; 5,248,793; 5,280,126; 5,397,792; and 5,342,952, which are herein incorporated by reference, disclose various processes and key intermediates for preparing atorvastatin.

Atorvastatin is prepared as its calcium salt, i.e., [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1). The calcium salt is desirable since it enables atorvastatin to be conveniently formulated in, for example, tablets, capsules, lozenges, powders, and the like for oral administration.

Concurrently filed U.S. patent applications titled "Crystalline [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic Acid Calcium Salt (2:1)"and" Form III Crystalline [R—(R*,R*)]-2-(4-fluorophenyl)-β,δ-dihydroxy-5-(1-methylethyl)-3-phenyl-4-[(phenylamino) carbonyl]-1H-pyrrole-1-heptanoic Acid Calcium Salt (2:1)" commonly owned, Ser. No. 08/945,812 now U.S. Pat. No. 5,969,156, and, Ser. No. 08/945,817, abandoned, disclose atorvastatin in various new crystalline forms designated Form I, Form II, Form III, and Form IV.

Atorvastatin disclosed in the above United States Patents is an amorphous solid. We have found that after the advent of crystalline atorvastatin, the production of amorphous atorvastatin by the previously disclosed processes was not consistently reproducible.

It has been disclosed that the amorphous forms in a number of drugs exhibit different dissolution characteristics and in some cases different bioavailability patterns compared to the crystalline form (Konno T., *Chem. Pharm. Bull.*, 1990;38:2003–2007). For some therapeutic indications one bioavailability pattern may be favored over another. Therefore, it is desirable to have a procedure for converting the crystalline form of a drug to the amorphous form.

The object of the present invention is a process which is amenable to large-scale production for converting crystalline Form I atorvastatin into amorphous atorvastatin.

We have surprisingly and unexpectedly found that solutions of atorvastatin in a non-hydroxylic solvent afford, after removal of the solvent, amorphous atorvastatin.

SUMMARY OF THE INVENTION

Accordingly, the present invention is a novel process for the preparation of amorphous atorvastatin and hydrates thereof which comprises:

(a) dissolving crystalline Form I atorvastatin in a non-hydroxylic solvent; and (b) removing the solvent to afford amorphous atorvastatin.

In a preferred embodiment of the invention, the non-hydroxylic solvent is selected from the group consisting of: tetrahydrofuran, and mixtures of tetrahydrofuran and toluene.

In another preferred embodiment of the invention, the solvent is removed in a vacuum dryer.

BRIEF DESCRIPTION OF THE DRAWINGS

The invention is further described by the following non-limiting examples which refer to the accompanying FIGS. 1, 2, and 3, short particulars of which are given below.

DETAILED DESCRIPTION OF THE INVENTION

Figure 1:
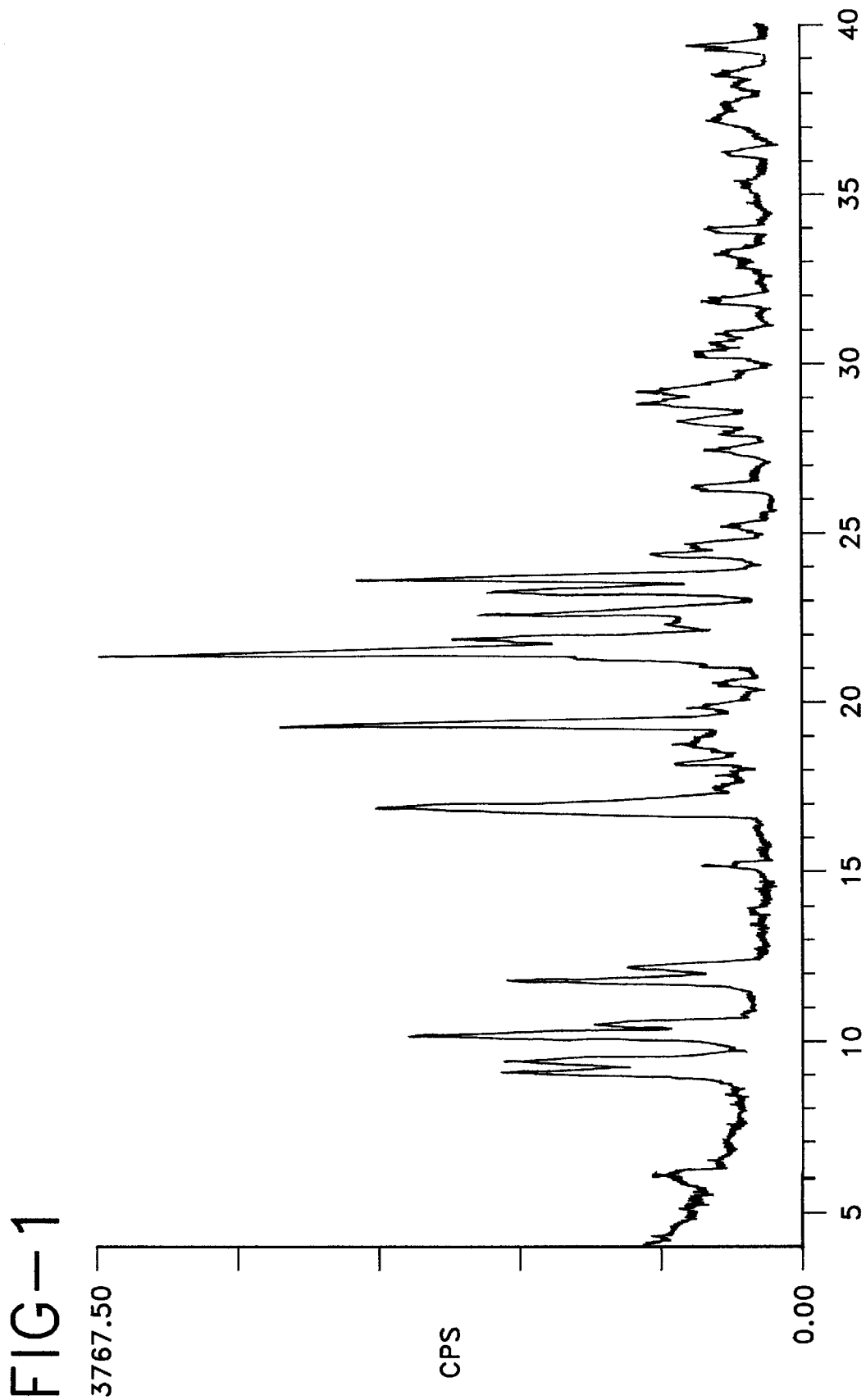
FIG. 1 Diffractogram of Form I atorvastatin ground for 2 minutes (Y-axis=0 to maximum intensity of 3767.50 counts per second(cps)).
Figure 2:
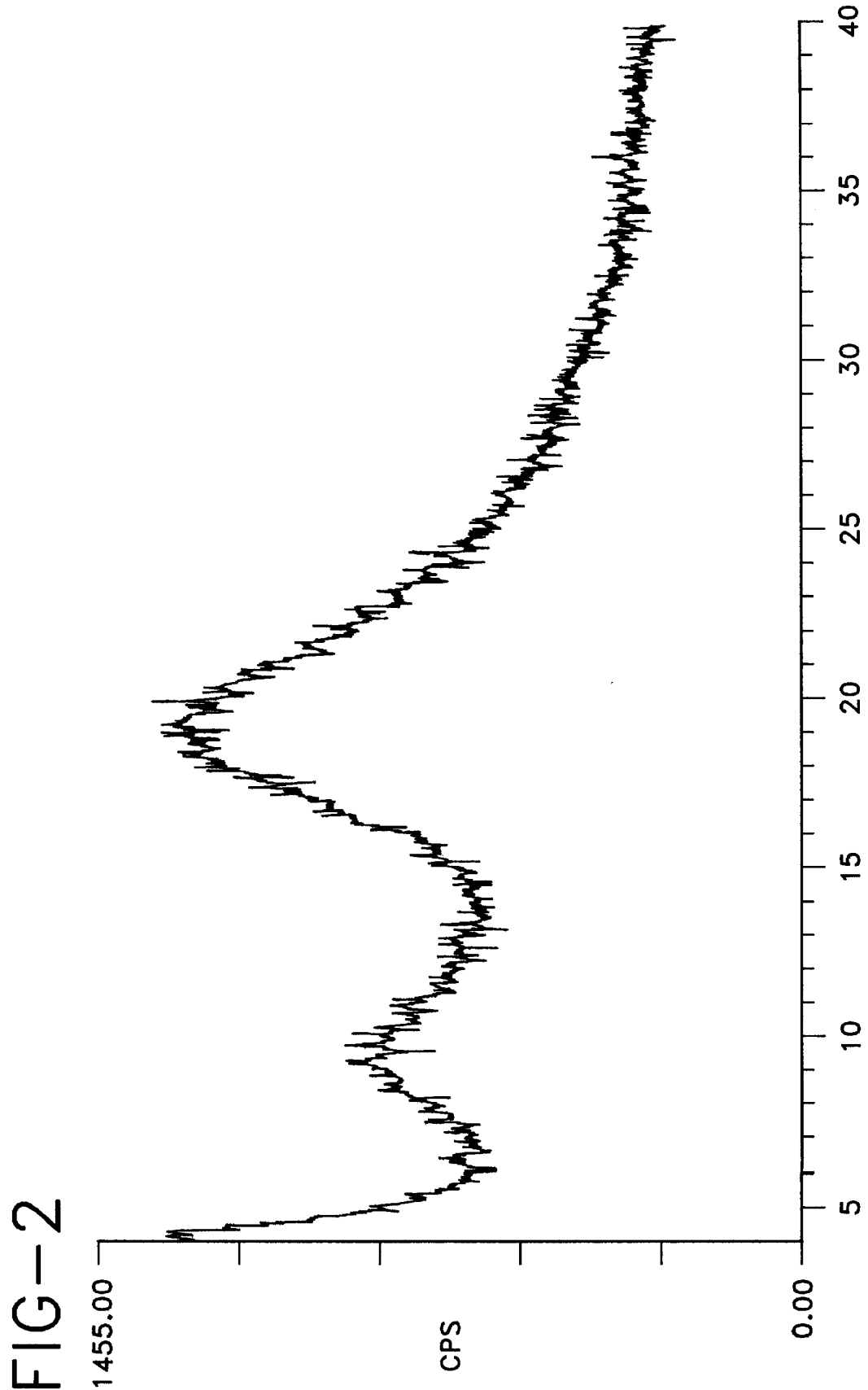
FIG. 2 Diffractogram of amorphous atorvastatin (Y-axis=0 to maximum intensity of 1455.00 cps).
Figure 3:
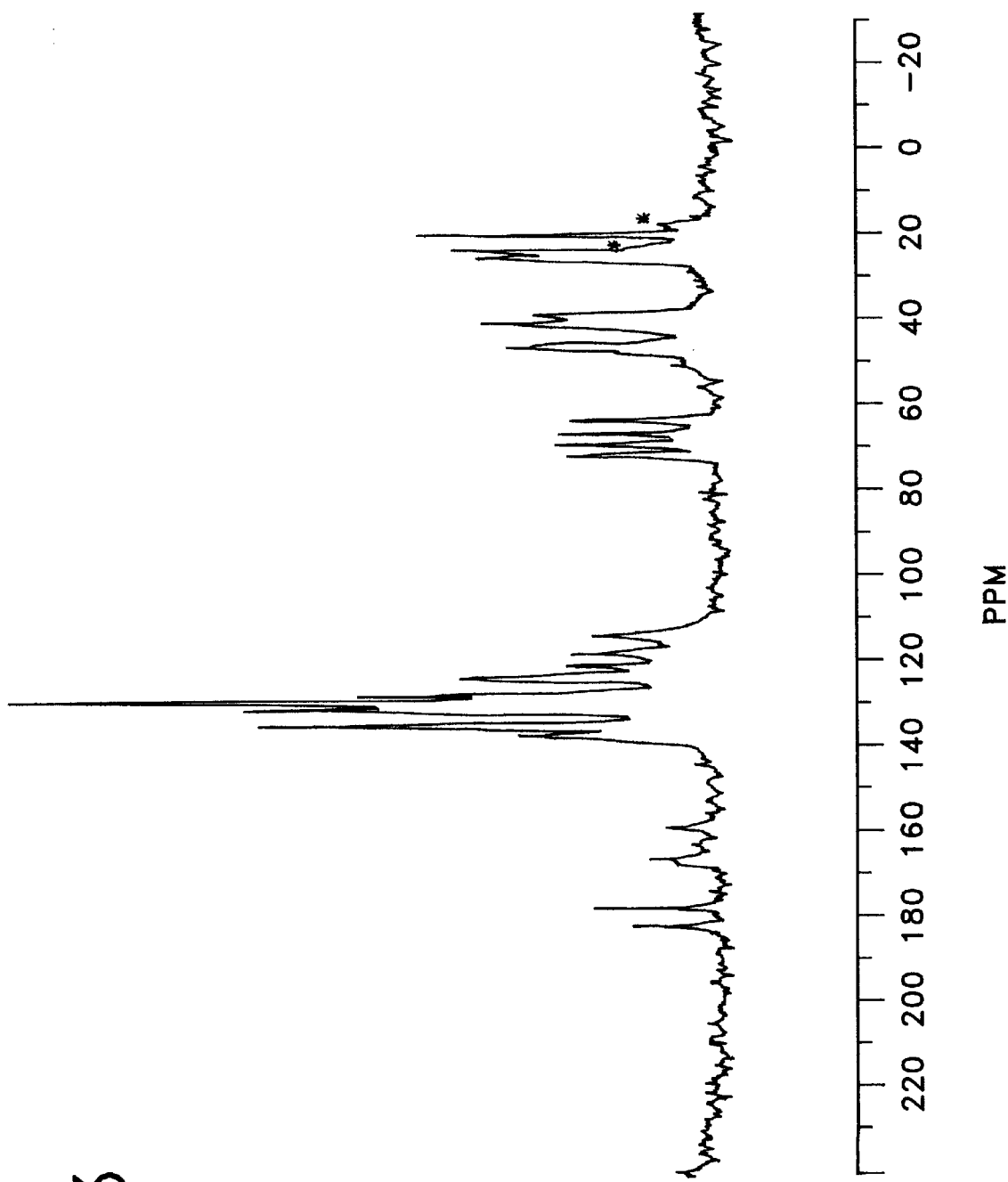
FIG. 3 Solid-state $^{13}$C nuclear magnetic resonance spectrum with spinning side bands identified by an asterisk of Form I atorvastatin.

Crystalline Form I atorvastatin may be characterized by its X-ray powder diffraction pattern and/or by its solid state nuclear magnetic resonance spectrum (NMR).

X-ray Powder Diffraction

Amorphous and Form I Atorvastatin

Amorphous and Form I atorvastatin were characterized by their X-ray powder diffraction patterns. Thus, the X-ray diffraction patterns of amorphous and Form I atorvastatin were measured on a Siemens D-500 diffractometer with CuK$_a$ radiation.

Equipment

Siemens D-500 Diffractometer-Kristalloflex with an IBM-compatible interface, software=DIFFRAC AT (SOCABIM 1986, 1992).

CuK$_a$ radiation (20 mA, 40 kV, λ=1.5406 Å) Slits I and II at 1° electronically filtered by the Kevex Psi Peltier Cooled Silicon [Si(Li)]Detector (Slits: III at 1° and IV at 0.15° ).

Methodology

The silicon standard is run each day to check the X-ray tube alignment.

Continuous θ/2θcoupled scan: 4.00° to 40.00° in 2θ, scan rate of 6°/min: 0.4 sec/0.04° step (scan rate of 3°/min: 0.8 sec/0.04° step for amorphous atorvastatin).

Sample tapped out of vial and pressed onto zero-background quartz in aluminum holder. Sample width 13–15 mm (sample width ~16 mm for amorphous atorvastatin).

Samples are stored and run at room temperature.

Grinding

Grinding is used to minimize intensity variations for the diffractogram of Form I atorvastatin disclosed herein. However, if grinding significantly altered the diffractogram or increased the amorphous content of the sample, then the diffractogram of the unground sample was used.

Table 1 lists the 2θ, d-spacings, and relative intensities of all lines in the unground sample with a relative intensity of >20% for crystalline Form I atorvastatin. Table 1 also lists the relative intensities of the same lines in a diffractogram measured after 2 minutes of grinding. The intensities of the sample ground for 2 minutes are more representative of the diffraction pattern without preferred orientation. It should also be noted that the computer-generated, unrounded numbers are listed in this table.

TABLE 1

Intensities and Peak Locations of all Diffraction Lines With Relative Intensity Greater Then 20% for Form I Atorvastatin

| 2θ | d | Relative Intensity (>20%) No Grinding | Relative Intensity (>20%)* Ground 2 Minutes |
|---|---|---|---|
| 9.150 | 9.6565 | 37.42 | 42.60 |
| 9.470 | 9.3311 | 46.81 | 41.94 |
| 10.266 | 8.6098 | 75.61 | 55.67 |
| 10.560 | 8.3705 | 24.03 | 29.33 |
| 11.853 | 7.4601 | 55.16 | 41.74 |
| 12.195 | 7.2518 | 20.03 | 24.62 |
| 17.075 | 5.1887 | 25.95 | 60.12 |
| 19.485 | 4.5520 | 89.93 | 73.59 |
| 21.626 | 4.1059 | 100.00 | 100.00 |
| 21.960 | 4.0442 | 58.64 | 49.44 |
| 22.748 | 3.9059 | 36.95 | 45.85 |
| 23.335 | 3.8088 | 31.76 | 44.72 |
| 23.734 | 3.7457 | 87.55 | 63.04 |
| 24.438 | 3.6394 | 23.14 | 21.10 |
| 28.915 | 3.0853 | 21.59 | 23.42 |
| 29.234 | 3.0524 | 20.45 | 23.36 |

*The second relative intensity column gives the relative intensities of the diffraction lines on the original diffractogram after 2 minutes of grinding.

Solid State Nuclear Magnetic Resonance (NMR) Methodology

All solid-state $^{13}$C NMR measurements were made with a Bruker AX-250, 250 MHz NMR spectrometer. High resolution spectra were obtained using high-power proton decoupling and cross-polarization (CP) with magic-angle spinning (MAS) at approximately 5 kHz. The magic-angle was adjusted using the Br signal of KBr by detecting the side bands as described by Frye and Maciel (Frye J. S. and Maciel G. E., *J. Mag. Res.*, 1982;48:125). Approximately 300 to 450 mg of sample packed into a canister-design rotor was used for each experiment. Chemical shifts were referenced to external tetrakis (trimethylsilyl)silane (methyl signal at 3.50 ppm) (Muntean J. V. and Stock L. M., *J. Mag. Res.*, 1988;76:54).

Table 2 shows the solid-state spectrum for crystalline Form I atorvastatin.

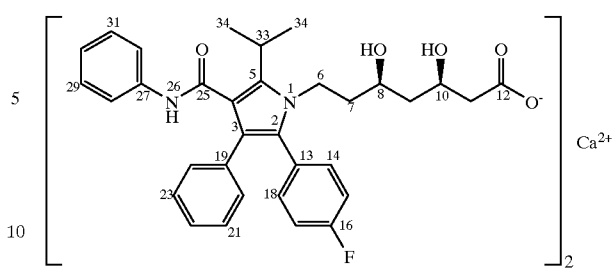

TABLE 2

Carbon Atom Assignment and Chemical Shift for Form I Atovastatin

| Assignment (7 kHz) | Chemical Shift |
|---|---|
| C12 or C25 | 182.8 |
| C12 or C25 | 178.4 |
| C16 | 166.7 (broad) and 159.3 |
| Aromatic Carbons | 137.0 |
| C2–C5, C13–C18, C129–C24, | 134.9 |
| C27–C32 | 131.1 |
|  | 129.5 |
|  | 127.6 |
|  | 123.5 |
|  | 120.9 |
|  | 118.2 |
|  | 113.8 |
| C8, C10 | 73.1 |
|  | 70.5 |
|  | 68.1 |
|  | 64.9 |
| Methylene Carbons | 47.4 |
| C6, C7, C9, C11 | 41.9 |
|  | 40.2 |
| C33 | 26.4 |
|  | 25.2 |
| C34 | 21.3 |

Amorphous atorvastatin of the present invention can exist in anhydrous forms as well as hydrated forms. In general, the hydrated forms, are equivalent to anhydrous forms and are intended to be encompassed within the scope of the present invention.

As previously described, amorphous atorvastatin is useful as an inhibitor of the enzyme, HMG-CoA reductase and is thus useful as a hypolipidemic and hypocholesterolemic agent.

The present invention provides a process for the commercial preparation of amorphous atorvastatin.

Thus, crystalline Form I atorvastatin is dissolved in a non-hydroxylic solvent such as, for example, tetrahydrofuran, mixtures of tetrahydrofuran and toluene and the like at a concentration of about 25% to about 40%. Preferably, crystalline Form I atorvastatin is dissolved in tetrahydrofuran at a concentration of about 25% to about 40% containing up to about 50% toluene as a co-solvent. The solvent is removed using, for example, drying technology such as, for example, vacuum drying, spray drying, and the like. Preferably, the drying procedure uses an agitated pan dryer such as, for example, Comber Turbodry Vertical Pan Dryer and the like. Drying initially is carried out at about 20° C. to about 40° C. and subsequently at about 70° C. to about 90° C. under vacuum at about 5 mm Hg to about 25 mm Hg for about 3 to about 5 days. Preferably, initial drying is carried out at about 35° C. and subsequently at about 85° C. at about 5 mm Hg to about 25 mm Hg for about 5 days. The initial solution dries to a brittle foam that is broken up by mechanical agitation to afford amorphous atorvastatin.

The following nonlimiting examples illustrate the inventors' preferred methods for preparing the compounds of the invention.

EXAMPLE 1

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid hemi calcium salt (Form I Atorvastatin)

A mixture of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (atorvastatin lactone) (U.S. Pat. No. 5,273,995) (75 kg), methyl tertiary-butyl ether (MTBE) (308 kg), methanol (190 L) is reacted with an aqueous solution of sodium hydroxide (5.72 kg in 950 L) at 48–58° C. for 40 to 60 minutes to form the ring-opened sodium salt. After cooling to 25–35° C., the organic layer is discarded, and the aqueous layer is again extracted with MTBE (230 kg). The organic layer is discarded, and the MTBE saturated aqueous solution of the sodium salt is heated to 47–52° C. To this solution is added a solution of calcium acetate hemihydrate (11.94 kg) dissolved in water (410 L), over at least 30 minutes. The mixture is seeded with a slurry of crystalline Form I atorvastatin (1.1 kg in 11 L water and 5 L methanol) shortly after addition of the calcium acetate solution. The mixture is then heated to 51–57° C. for at least 10 minutes and then cooled to 15–40° C. The mixture is filtered, washed with a solution of water (300 L) and methanol (150 L) followed by water (450 L). The solid is dried at 60–70° C. under vacuum for 3 to 4 days to give crystalline Form I atorvastatin (72.2 kg).

EXAMPLE 2

[R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt (Amorphous Atorvastatin)

Crystalline Form I atorvastatin (Example 1) (30 kg) is dissolved with agitation in tetrahydrofuran (75 L) at ambient temperature under a nitrogen atmosphere. Toluene (49.4 L) is added slowly once solution is achieved. The solution is then transferred through a 0.45 micron Pall filter to a 200 L Comber Turbodry Vertical Pan Dryer. The transfer system is rinsed to the dryer with additional tetrahydrofuran (4.5 L). Full vacuum is applied, and the solution is concentrated at 35° C. with mild agitation. Near the end of the concentration process, the agitator is lifted. The product turns into a brittle glassy foam. The agitator is gradually lowered, breaking the brittle foam into a free flowing powder. The powder is agitated and the temperature is raised to 85° C. under vacuum (6 to 8 mm Hg) to lessen the residual solvent levels. After 4 days of drying, the desired residual solvent levels of 0.01% tetrahydrofuran and 0.29% toluene are achieved. The free flowing white powder (27.2 kg) is unloaded from the dryer. The product is amorphous by X-ray powder diffraction.

What is claimed is:

1. A process for the preparation of amorphous atorvastatin or hydrates thereof which comprises:
    (a) dissolving crystalline Form I atorvastatin having the formula

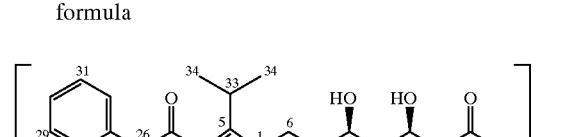
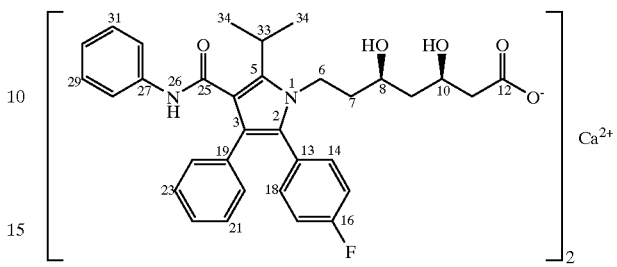

in a non-hydroxylic solvent at a concentration of about 25% to about 40%; and
    (b) removing the solvent by drying to afford said amorphous atorvastatin or hydrates thereof.

2. A process for the preparation of anhydrous amorphous atorvastatin which comprises:
    (a) dissolving crystalline Form I atorvastatin having the formula in a non-hydroxylic solvent at a concentration of about 25% to about 40%; and
    (b) removing the solvent by drying to afford said anhydrous amorphous atorvastatin.

3. A process for the preparation of hydrated amorphous atorvastatin which comprises:
    (a) dissolving crystalline Form I atorvastatin having the formula in a non-hydroxylic solvent at a concentration of about 25% to about 40%; and
    (b) removing the solvent by drying to afford said hydrated amorphous atorvastatin.

* * * * *